(12) United States Patent
Kim et al.

(10) Patent No.: US 8,036,849 B2
(45) Date of Patent: Oct. 11, 2011

(54) MODULE FOR MEASURING PHYSICAL ATTRIBUTES LINKED TO EXERCISE, SYSTEM FOR ANALYZING PHYSICAL ATTRIBUTES LINKED TO EXERCISE AND INCLUDING THE MODULE, AND METHOD OF APPLYING THE MODULE

(75) Inventors: Youn-ho Kim, Hwaseong-si (KR);
Woo-young Jang, Seongnam-si (KR);
Kun-soo Shin, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 214 days.

(21) Appl. No.: 12/169,862

(22) Filed: Jul. 9, 2008

(65) Prior Publication Data
US 2009/0150113 A1 Jun. 11, 2009

(30) Foreign Application Priority Data
Dec. 6, 2007 (KR) .................. 10-2007-0126379

(51) Int. Cl.
*G06F 15/00* (2006.01)

(52) U.S. Cl. .......... 702/127; 345/156; 600/300; 607/59; 702/32; 705/2

(58) Field of Classification Search ............... 702/74, 702/96, 104, 106, 116, 127, 141, 183, 188, 702/189, 32; 600/300, 301; 607/59; 340/539.12; 705/2; 345/156
See application file for complete search history.

(56) References Cited

U.S. PATENT DOCUMENTS

| | | | | |
|---|---|---|---|---|
| 6,088,017 A * | 7/2000 | Tremblay et al. | ............. | 345/156 |
| 2004/0117212 A1* | 6/2004 | Kong et al. | ............. | 705/2 |
| 2005/0192488 A1* | 9/2005 | Bryenton et al. | ............. | 600/301 |
| 2008/0188909 A1* | 8/2008 | Bradley | ............. | 607/59 |
| 2008/0312511 A1* | 12/2008 | Osler et al. | ............. | 600/300 |

* cited by examiner

*Primary Examiner* — John H Le
*(74) Attorney, Agent, or Firm* — Sughrue Mion, PLLC

(57) ABSTRACT

A module for measuring physical attributes linked to includes a pad that is attachable or wearable to the body of a person; a signal sensing unit installed on the pad to sense at least one type of physical attributes signal that changes according to motions of the body; and a transmitting unit transmitting the physical attributes signal sensed by the signal sensing unit. A system including the module and a method of applying the module is also provided.

16 Claims, 7 Drawing Sheets

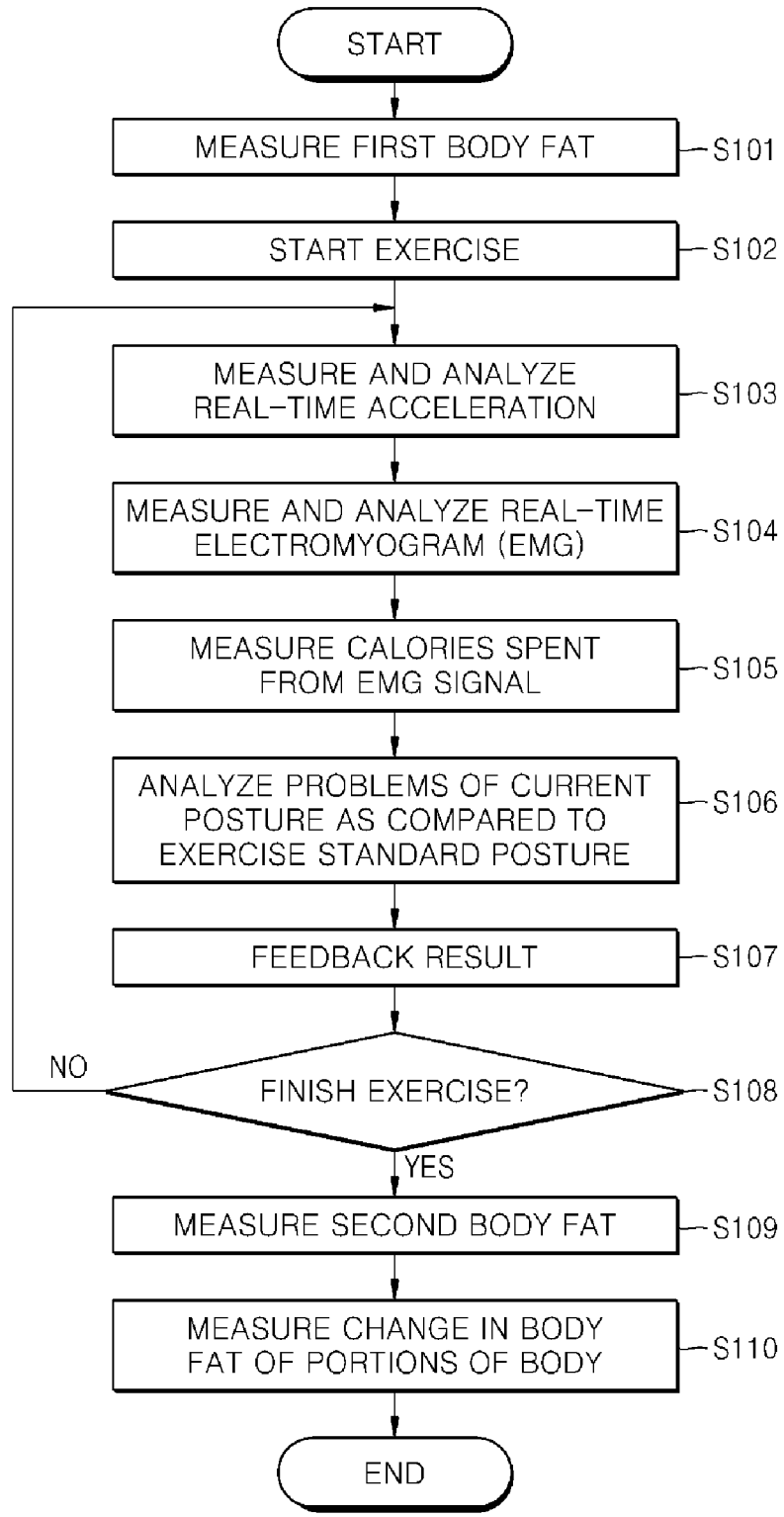

MODULE FOR MEASURING PHYSICAL ATTRIBUTES LINKED TO EXERCISE, SYSTEM FOR ANALYZING PHYSICAL ATTRIBUTES LINKED TO EXERCISE AND INCLUDING THE MODULE, AND METHOD OF APPLYING THE MODULE

CROSS-REFERENCE TO RELATED PATENT APPLICATION

This application claims the benefit of Korean Patent Application No. 10-2007-0126379, filed on Dec. 6, 2007 in the Korean Intellectual Property Office, the disclosure of which is incorporated herein in its entirety by reference.

BACKGROUND OF THE INVENTION

1. Field of the Invention

The present invention relates to an analysis of physical attributes linked to exercise by a person, and more particularly, to a module capable of measuring physical attributes linked to exercise and which vary from person to person, by wearing or attaching the module during exercising, a system including the module, and a method of applying the module to correct the posture for sports or overall fitness, to lose weight, or to stay fit, and so on.

2. Description of the Related Art

Until now, individuals have been able to learn certain sports such as golf or tennis through the help of an instructor, by themselves, or by competing against others. In order for a person to improve their skills once the basics of the sports have been learned, the posture of the person still needs to be corrected while playing the sport. However, such posture is usually analyzed by reviewing the postures through video, or through the analysis of an instructor presently viewing the posture first hand, so as to correct the posture. Accordingly, it is not easy to observe and recognize small posture errors, and comments to correct the posture errors based on the analysis of the posture since such analysis can be subjective, thus decreasing the efficiency of correcting the posture.

Also, the health goals of the person may differ from person to person. In other words, some people may want to tone muscles or increase muscle strength, while other people may want to get into shape, lose weight, or slim down certain body parts. However, there is no way to quantitatively figure out what kind of sports or which type of exercise motion is suitable for a particular health goal of an individual.

SUMMARY OF THE INVENTION

The present invention provides a module that is attachable to the body of a person, and for measuring signals related to physical attributes linked to exercise that change according to motions of the body in real-time, a system for analyzing the physical attributes linked to exercise and including the module, and a method of applying the module for measuring physical attributes linked to exercise.

According to an aspect of the present invention, there is provided a module for measuring physical attributes linked to exercise, the module comprising: a pad that that is attachable or wearable to the body of a person; a signal sensing unit installed in the pad to sense at least one type of physical attributes signal that changes according to motions of the body; and a transmitting unit transmitting the physical attributes signal sensed by the signal sensing unit.

According to another aspect of the present invention, there is provided a system for analyzing physical attributes linked to exercise, the system comprising: at least one of the above-described module; and a signal analyzer comprising: a receiving unit receiving the transmitted physical attributes signal; an analyzing unit analyzing physical attributes of the person; and a result feedback unit notifying the person of the analysis result.

The signal sensing unit may be embodied to sense an electromyogram (EMG) signal, an acceleration signal, or a body fat signal.

The signal sensing unit may include at least a pair of electromyogram (EMG) measuring electrodes for measuring an EMG signal, or at least a pair of body fat measuring electrodes for measuring a body fat signal, the EMG and body fat measuring electrodes being attachable to the body for sensing signals.

The pad may be long enough to correspondingly surround a preset body portion, and flexible enough to be closely conformable to attach to curved or angled body portions.

The system may comprise a plurality of the modules for measuring physical attributes linked to exercise so as to sense physical attributes signals at various body portions.

The analyzing unit may determine whether or not a posture is correct, measure change in body fat due to exercise, or measure calories spent through exercising.

The result feedback unit may notify the person of the analysis result using images, sound, or vibration.

According to another aspect of the present invention, there is provided a method of applying a module, for measuring physical attributes linked to exercise, comprising: a pad that is attachable or wearable to the body of a person; a signal sensing unit installed in the pad to sense at least one type of physical attributes signal that changes according to motions of the body; and a transmitting unit transmitting the physical attributes signal sensed by the signal sensing unit, the method comprising: attaching or wearing the module on a preset body portion; exercising while having the module attached to the body; sensing at least one physical attributes signal changing through exercising; and analyzing the physical attributes of a person by receiving the sensed physical attributes signal and analyzing the sensed physical attributes signal.

The physical attributes signal may include an electromyogram signal, and the sensing of the physical attributes signal may include consecutively sensing electromyogram signals changing during exercising, and the analyzing of the physical attributes may include determining whether the posture of the person is correct based on the electromyogram signals, or measuring the calories spent based on the electomygrogram signals.

The physical attributes signal may include an electromyogram signal and an acceleration signal, and the sensing of the physical attributes signal may include consecutively sensing electromyogram signals and acceleration signals changing during exercising, and the analyzing of the physical attributes may include determining whether the posture of the person is correct, based on the electromyogram signal and the acceleration signal.

The physical attributes signal may include a body fat signal, and the sensing of the physical attributes signal may include sensing body fat signals before and after exercising, and the analyzing of the physical attributes may include measuring a difference in the body fat due to the exercising based on the difference in the body fat signals before and after exercising.

The attaching or wearing of the module may include attaching or wearing a plurality of the modules on the body of the person so that physical attribute signals can be sensed at various body portions.

BRIEF DESCRIPTION OF THE DRAWINGS

The above and other features and advantages of the present invention will become more apparent by describing in detail exemplary embodiments thereof with reference to the attached drawings in which:

FIG. 4 is a flowchart illustrating a method of applying the module, according to an embodiment of the present invention;

DETAILED DESCRIPTION OF THE INVENTION

The present invention will now be described more fully with reference to the accompanying drawings, in which exemplary embodiments of the invention are shown.

Figure 1:
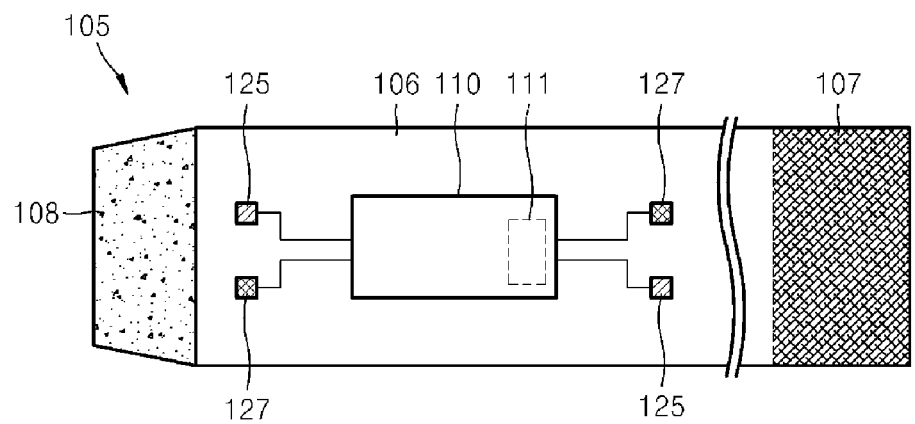
FIG. 1 is a plane view of a module for measuring physical attributes linked to exercise, according to an embodiment of the present invention.
Figure 2:
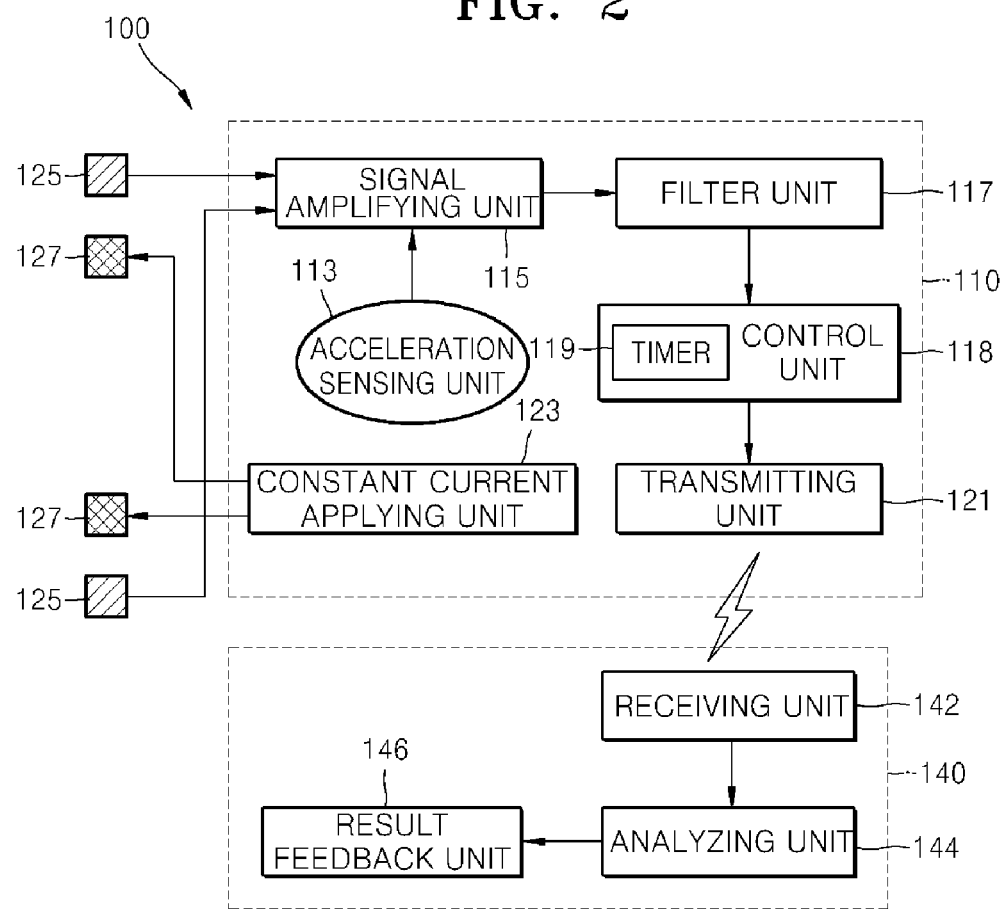
FIG. 2 is a diagram of a system for analyzing physical attributes linked to exercise, according to an embodiment of the present invention.
Figure 3:
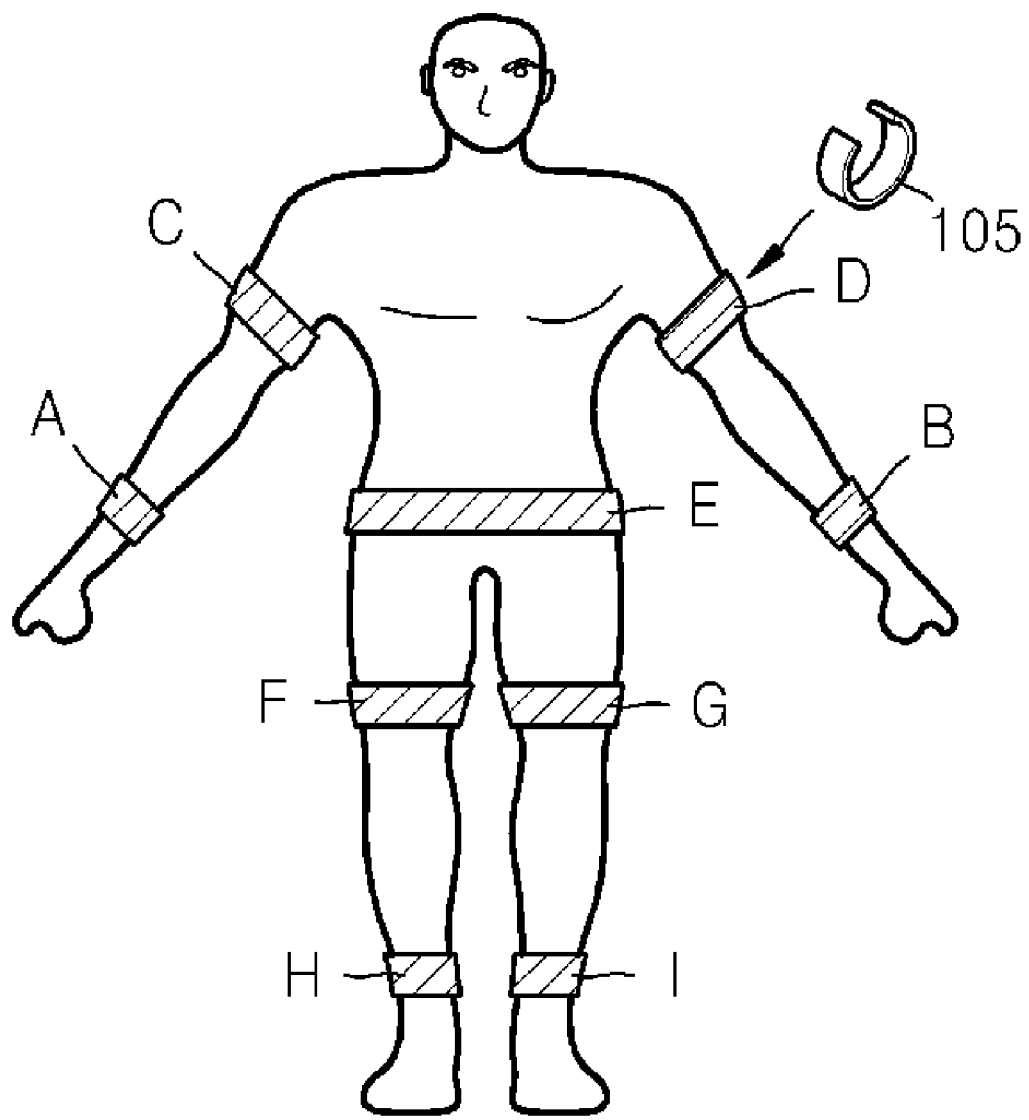
FIG. 3 is a front view of an examinee wearing the module, according to an embodiment of the present invention.
Figure 5A:
FIGS. 5A through 5D illustrate postures of a golf swing stepwise.
Figure 5B:
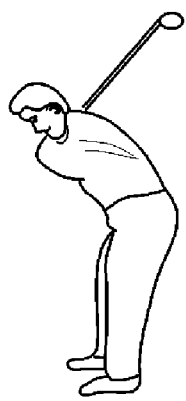
Figure 5C:
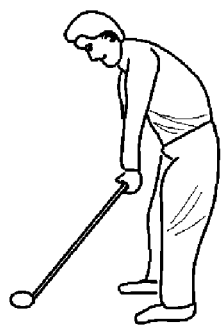
Figure 5D:

FIG. 1 is a plane view of a module 105 for measuring physical attributes linked to exercise, according to an embodiment of the present invention. FIG. 2 is a diagram of a system 100 for analyzing physical attributes linked to exercise, according to an embodiment of the present invention. FIG. 3 is a front view of an examinee wearing the module 105, according to an embodiment of the present invention.

Referring to FIGS. 1 and 2, the system 100 includes a module 105, which is attachable to the body of a person, to sense physical attributes signals during exercising, and a signal analyzer 140 receiving the sensed physical attributes signals and analyzing the sensed physical attributes signals, and notifying the person of the result of the analysis. The module 105 includes a pad 106 that can be wearable to the body, a hardware package 110 installed on the pad 106, and two pairs of electrodes 125 and 127 that are wire-connected to the hardware package 110.

Referring to FIGS. 1 and 3, the pad 106 is flexible enough to be closely conformable to curved or angled body portions, and long enough to correspondingly surround a preset body portion. In addition, the system 100 includes a plurality of the modules 105 in order to sense physical attributes signals during exercising at various body portions A through I; for example, a pad 106 of the module 105 on the waist E is longer than pads 106 of the modules 105 on the forearms C and D; and pads 106 of the modules 105 on the thighs F and G are shorter than a pad 106 of the module 105 on the waist E and longer than pads 106 of the modules 105 on the forearms C and D.

In FIG. 1, first and second end portions 107 and 108 of the pad 106 can be separably attached using a Velcro tape. In detail, a Velcro loop surface is formed on the first end portion 107 of the pad 106, and a Velcro hook surface is formed on the second end portion 108 of the pad 106, which is opposite to the first end portion 107. Accordingly, when wearing the module 105, the pad 106 correspondingly surrounds a predetermined body portion, so as to not disattach from the body, and can be easily disattached after exercising. However, the present invention is not limited to the module 105, and thus, other modules including pads attachable on predetermined body portions using an adhesive agent may belong to the present invention.

Referring to FIGS. 1 and 2, the hardware package 110 includes units constituting a signal sensing unit sensing three types of physical attributes signals that vary according to motions of the body, that is, an acceleration signal, an electromyogram (EMG) signal, and a body fat signal, a transmitting unit 121 transmitting the physical attributes signals that are sensed by the signal sensing unit, and a battery 111 for supplying power to each of the units in the hardware package 110.

Among the two pairs of the electrodes 125 and 127, the one pair of the electrodes 125 are EMG measuring electrodes sensing an EMG signal, and the other pair of the electrodes 127 are body fat measuring electrodes sensing a body fat signal. The EMG measuring electrodes 125 and the body fat measuring electrodes 127 are attached to the body for sensing a body potential signal, and the two pairs of the electrodes 125 and 127 are included in the signal sensing unit.

As the units constituting the signal sensing unit, an acceleration sensing unit 113, a signal amplifying unit 115, a filter unit 117, a control unit 118, a timer 119, and a constant current applying unit 123 are included in the hardware package 110. The acceleration sensing unit 113 senses acceleration signals to measure position information of the body portion, on which the module 105 is worn, according to time. The signal amplifying unit 115 amplifies physical attributes signals during exercising, that is, the EMG signal sensed by the EMG measuring electrodes 125, body fat signals sensed by the body fat measuring electrodes 127, and acceleration signals sensed by the acceleration sensing unit 113. The filter unit 117 filters the sensed EMG signals within a preset EMG frequency band to extract EMG wave forms. The control unit 118 collects the sensed physical attributes signals. The timer 119 records the time the physical attributes signals are sensed. The constant current applying unit 123 applies constant current, in the form of a sinusoidal wave once before and once after exercising so as to sense the body fat signals, to the body fat measuring electrodes 127. Also, the transmitting unit 121 transmits the sensed physical attributes signals to the signal analyzer 140 including a receiving unit 142, an analyzing unit 144, and a result feedback unit 146. The receiving unit 142 receives physical attributes signals transmitted from the module 105. In FIG. 2, communication between the transmitting unit 121 and the receiving unit 142 is wireless; however, the present invention is not limited thereto, and thus, communication between the transmitting unit 121 and the receiving unit 142 is possible in a wired manner.

The analyzing unit 144 analyzes physical attributes linked to exercise by a person using the received physical attributes signals. For example, the analyzing unit 144 can analyze physical attributes linked to exercise by a person such as, whether a posture of an exercise is correct, how much body fat measurements change due to exercise, or how much calories are spent through exercise. A detailed analyzing method of physical attributes related to exercise by a person will be described later. The result feedback unit 146 notifies the person of the analysis result of the analyzing unit 144. For example, the result feedback unit 146 can notify the person of the analysis result using images such as graphs, numbers, letters displayed on a display screen, or voice or horn sound, or vibration of the signal analyzer 140.

Hereinafter, a method of applying the module 105 will be described.

Figure 6A:
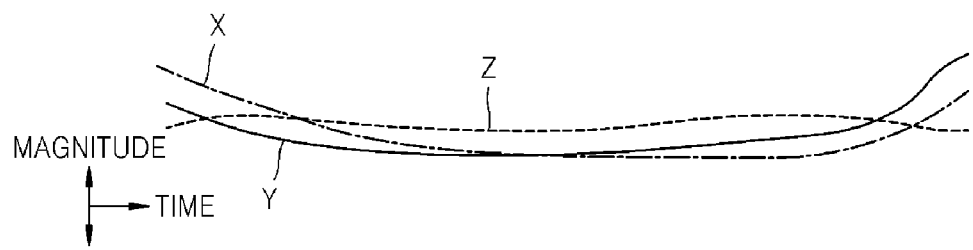
FIG. 6A is a graph illustrating acceleration during a golf swing of an examinee correcting their golf swing posture.
Figure 6B:
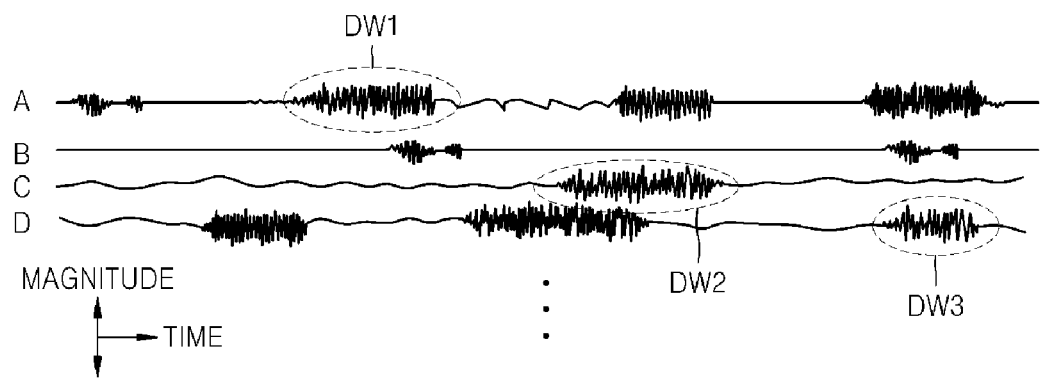
FIG. 6B is a graph illustrating an electromyogram (EMG) during a golf swing of an examinee correcting their golf swing posture.
Figure 7:
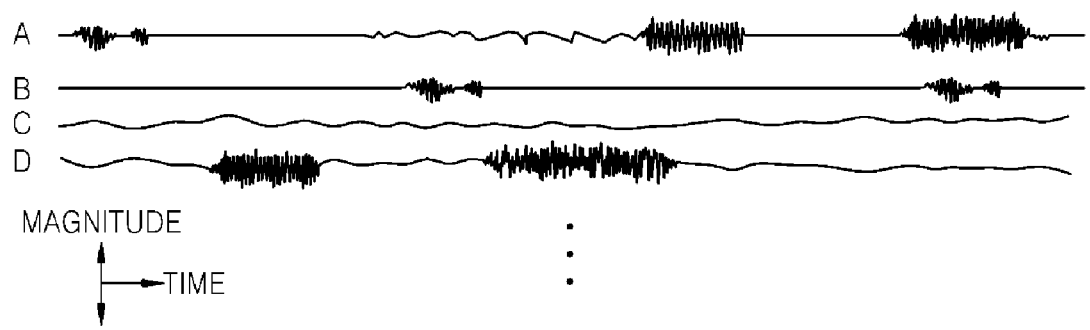
FIG. 7 is a graph showing EMG of a golf swing expert making a golf swing as the standard for correcting of a golf swing posture.
Figure 8A:
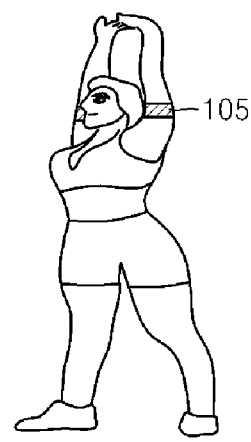
FIGS. 8A through 8C illustrate stretching exercises.
Figure 8B:
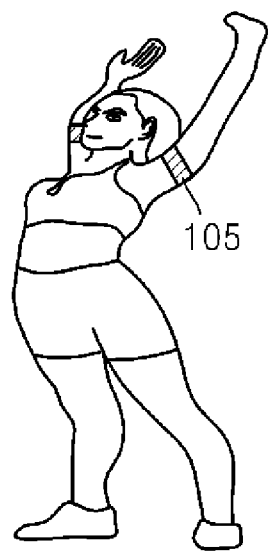
Figure 8C:

FIG. 4 is a flowchart illustrating the method of applying the module 105, according to an embodiment of the present invention. FIGS. 5A through 5D illustrate a golf swing posture stepwise. FIG. 6A is a graph illustrating acceleration during a golf swing of an examinee correcting their golf swing posture. FIG. 6B is a graph of EMG during a golf swing of an examinee correcting their golf swing posture. FIG. 7 is a graph showing EMG of a golf swing expert making a golf swing as the standard for correcting of a golf swing posture. FIGS. 8A through 8C illustrate stretching exercises.

Using the module 105 according to the present invention, for example, postures of sports such as golf and tennis can be corrected, and changes in body fat of predetermined body portions, such as the forearms, during exercising and calories spent through the exercise can be measured. Hereinafter, as an example of applying the module 105, a method of correcting the golf swing posture will be described with reference to FIGS. 4 through 7.

First, as illustrated in FIG. 3, the modules 105 are worn on various body portions A through I of the examinee, for example, arms, legs, waist, etc., and then a first body fat is measured with respect to each of the body portions A through 1, in operation S101. As described above, body fat is measured by applying a constant current in the form of a sinusoidal form to the body fat measuring electrode 127 (see FIG. 2) using the constant current applying unit 123 (see FIG. 2) of the module 105, sensing a body fat signal as a response signal to the applied constant current using the body fat measuring electrode 127, and analyzing the sensed body fat signal using the analyzing unit 144 of the signal analyzer 140 (see FIG. 2).

Next, in operation S102, the examinee wearing the module 105 makes a golf swing. Such golf swing refers to a continuous process in which addressing (see FIG. 5A), a back swing (see FIG. 5B), a down swing and an impact (see FIG. 5C), and a follow through (see FIG. 5D) are sequentially performed. Acceleration and EMG are respectively measured and analyzed during such a golf swing in real-time, in operations S103 and S104. As described above, the acceleration is measured and analyzed by the analyzing unit 144 (see FIG. 2) of the signal analyzer 140 (see FIG. 2) analyzing the acceleration signal sensed by the acceleration sensing unit 113 (see FIG. 2) of the module 105, and the EMG is measured and analyzed by the analyzing unit 144 of the signal analyzer 140 analyzing the EMG signal sensed by the EMG measuring electrode 125.

An example of the acceleration measurement results can be displayed in a graph illustrating accelerations in three X, Y, and Z directions as illustrated in FIG. 6A for easy understanding. By combining the acceleration measurement results in the three X, Y, and Z directions, displacement of a predetermined body portion where the acceleration signals are sensed can be detected, and by combining all the acceleration measurement results measured using the module 105 that is worn on each body portion, a track of the body during a golf swing can be analyzed.

Also, an example of the EMG measurement results is shown in the graph of FIG. 6B, and such EMG measurement results involve an irregular wave with an intermittent period during which the irregular wave abruptly fluctuates. When a muscle contracts as force is applied by a predetermined body portion, the abruptly fluctuating portions of the irregular wave occur. In FIG. 6B, only a graph of the EMG measurement results of body portions A, B, C, and D (see FIG. 3) is illustrated, but it is obvious that such EMG measurement results can also be obtained for the other body portions E through I (see FIG. 3).

In operation S105, calories spent due to making a golf swing is measured based on the results of measurement of the EMG measurement results. The process of measuring the calories spent may include a process of integrating the waves that resulted from the EMG measurement results. Next, in operation S106, the posture problems of the examinee are analyzed by comparing the EMG measurement results and the acceleration measurement results with standard posture data, that is, reference EMS measurement results and reference acceleration measurement results obtained from the golf swing of an expert.

In other words, the examinee can compare their acceleration measurement results (see FIG. 6A) with the reference acceleration measurement results (not shown) to find out how their track of the golf swing differs from that of an expert, and thus try to make their posture correspond to that of the expert. Also, the examinee can compare their EMG measurement results (see FIG. 6B) with the reference EMG measurement results obtained from a reference golf swing (see FIG. 7) to find out body portions that are strained needlessly or body portions to which force is improperly applied and thus try to make corrections accordingly. For example, in FIG. 6B, the abruptly fluctuating portions DW1, DW2, and DW3 which do not exist in FIG. 7 indicate that the golf swing of the examinee includes movements where the examinee needlessly feels nervous, unlike the golf swing of the expert. Accordingly, the examinee can easily find out their golf swing problems during their golf swing and can intentionally try to correct their golf swing problems.

The result feedback unit 146 (see FIG. 2) notifies the examinee of the analysis result of operations S103 through S105, in operation S107. If the reference acceleration measurement results and the reference EMG measurement results are stored in the signal analyzer 140 (see FIG. 2), the analyzing unit 144 can perform operation S106, and the analysis result of operation S106 can be notified to the examinee through the result feedback unit 146. As described above, the feedback of the result can be provided using images, sound, or vibration.

Next, in operation S108, it is determined whether an exercise is finished. Thus, if it is determined that the exercise is finished, a second body fat measurement is performed on the body portions A through I on which the module 105 is attached, in operation S109. In operation S109, the process of the second body fat measurement is the same as that of the first body fat measurement, and thus the description thereof will not be repeated. Next, in operation S10, the result of the second body fat measurement (operation S109) is abstracted from the result of the first body fat measurement (operation S101) to measure the change in the body fat of each of the body portions. If it is determined that the exercise is not finished in operation S108, operations S103 through S107 are repeated.

Hereinafter, another example of applying the module 105 to select exercise suitable for the health goal of an examinee will be described by taking stretching as an example, with reference to FIGS. 8A through 8C.

First, it is assumed that the examinee wants to do stretching in order to lose weight from the forearms to thereby improve their figure. Thus, the examinee first puts on a pair of the modules 105 on the forearms, and measures a first body fat before starting stretching. The process of measuring body fat is described above with reference to operation S101 of FIG. 4, and thus a description thereof will not be repeated. Then, after doing a first type of stretch as illustrated FIG. 8A, a second body fat is measured. The measurement result of the second body fat is abstracted from the measurement result of the first body fat to measure change in body fat by the first type of stretch.

In this way, like the measurement of the change in the body fat according to the first type of stretch, change in body fat after performing a second type of stretch, as illustrated in FIG. 8B, and change in body fat after performing a third type of stretch, as illustrated in FIG. 8C, are measured respectively. Then when the examinee compares the change in body fat of the three types of stretches to select one type from among the stretches that has the greatest change in body fat and continues exercising by doing the selected one, the health goal of the examinee can be achieved more easily. For example, if the value of the change in body fat of the forearms after the first and second types of stretches are 2 and the value of the change in body fat of the forearms after the third type of stretch is 5, the examinee can select the third type of stretch as the most effective one and continue exercising by doing the third type of stretch.

While the present invention has been particularly shown and described with reference to exemplary embodiments thereof, it will be understood by one of ordinary skill in the art that various changes in form and details may be made therein without departing from the spirit and scope of the present invention as defined by the following claims.

What is claimed is:

1. A module for measuring physical attributes linked to exercise, the module comprising:
   a pad that is attachable or wearable to the body of a person;
   a signal sensing unit installed in the pad to sense at least one type of physical attributes signal that changes according to motions of the body, wherein the signal sensing unit is embodied to sense an electromyogram (EMG) signal;
   a transmitting unit transmitting the physical attributes signal sensed by the signal sensing unit; and
   a signal analyzing unit which receives the transmitted physical attributes signal and determines whether or not a posture is correct by comparing the sensed EMG signal with a reference EMG measurement.

2. The module of claim 1, wherein the signal sensing unit is embodied to sense an acceleration signal or a body fat signal.

3. The module of claim 1, wherein the signal sensing unit includes at least a pair of electromyogram (EMG) measuring electrodes for measuring an EMG signal, or at least a pair of body fat measuring electrodes for measuring a body fat signal, the EMG and body fat measuring electrodes being attachable to the body for sensing signals.

4. The module of claim 1, wherein the pad is long enough to correspondingly surround a preset body portion, and flexible enough to be closely conformable to attach to curved or angled body portions.

5. A system for analyzing physical attributes linked to exercise, the system comprising:
   a module, for measuring physical attributes linked to exercise, comprising: a pad that is attachable or wearable to the body of a person; a signal sensing unit installed in the pad to sense at least one type of physical attributes signal that changes according to motions of the body, wherein the signal sensing unit is embodied to sense an electromyogram (EMG) signal; and a transmitting unit transmitting the physical attributes signal sensed by the signal sensing unit; and
   a signal analyzer comprising:
      a receiving unit receiving the transmitted physical attributes signal;
      an analyzing unit analyzing physical attributes of the person; and
      a result feedback unit notifying the person of the analysis result,
      wherein the analyzing unit determines whether or not a posture is correct by comparing the sensed EMG signal with a reference EMG measurement.

6. The system of claim 5, wherein the signal sensing unit is embodied to sense an acceleration signal, or a body fat signal.

7. The system of claim 5, wherein the signal sensing unit includes at least a pair of electromyogram (EMG) measuring electrodes for measuring an EMG signal, or at least a pair of body fat measuring electrodes for measuring a body fat signal, the EMG and body fat measuring electrodes being attachable to the body for sensing signals.

8. The system of claim 5, wherein the pad is long enough to correspondingly surround a preset body portion, and flexible enough to be closely conformable to attach to curved or angled body portions.

9. The system of claim 5, comprising a plurality of the modules for measuring physical attributes linked to exercise so as to sense physical attributes signals at various body portions.

10. The system of claim 5, wherein the analyzing unit measures change in body fat due to exercise, or measures calories spent through exercising.

11. The system of claim 5, wherein the result feedback unit notifies the person of the analysis result using images, sound, or vibration.

12. A method of applying a module, for measuring physical attributes linked to exercise, comprising: a pad that is attachable or wearable to the body of a person; a signal sensing unit installed in the pad to sense at least one type of physical attributes signal that changes according to motions of the body; and a transmitting unit transmitting the physical attributes signal sensed by the signal sensing unit, the method comprising:
   attaching or wearing the module on a preset body portion, exercising while having the module attached to the body;
   sensing at least one physical attributes signal changing through exercising; and
   analyzing the physical attributes of a person by receiving the sensed physical attributes signal and analyzing the sensed physical attributes signal,
   wherein the physical attributes signal includes an electromyogram (EMG) signal, and
   wherein the analyzing of the physical attributes includes determining whether the posture of the person is correct by comparing the sensed EMG signal with a reference EMG measurement.

13. The method of claim 12, wherein the sensing of the physical attributes signal includes consecutively sensing electromyogram signals changing during exercising, and the analyzing of the physical attributes includes determining whether the posture of the person is correct based on the electromyogram signals, or measuring the calories spent based on the electomygrogram signal.

14. The method of claim 12, wherein the physical attributes signal includes an electromyogram signal and an acceleration signal, and the sensing of the physical attributes signal includes consecutively sensing electromyogram signals and acceleration signals changing during exercising, and the analyzing of the physical attributes includes determining whether the posture of the person is correct, based on the electromyogram signal and the acceleration signal.

15. The method of claim 12, wherein the physical attributes signal includes a body fat signal, and the sensing of the physical attributes signal includes sensing body fat signals before and after exercising, and the analyzing of the physical attributes includes measuring a difference in the body fat due to the exercising based on the difference in the body fat signals before and after exercising.

16. The method of claim 12, wherein the attaching or wearing of the module includes attaching or wearing a plurality of the modules on the body of the person so that physical attribute signals can be sensed at various body portions.

* * * * *